US012589055B2

(12) United States Patent
Klee et al.

(10) Patent No.: US 12,589,055 B2
(45) Date of Patent: Mar. 31, 2026

(54) DENTAL COMPOSITION

(71) Applicant: DENTSPLY SIRONA Inc., York, PA (US)

(72) Inventors: Joachim E. Klee, Radolfzell (DE); Florian Szillat, Neukirchen-Vlyun (DE); Jacques Lalevée, Mulhouse (FR); Julie Kirschner, Dambach-la-Ville (FR); Fabrice Morlet-Savary, Pfastatt (FR)

(73) Assignee: Dentsply Sirona Inc., York, PA (US)

( * ) Notice: Subject to any disclaimer, the term of this patent is extended or adjusted under 35 U.S.C. 154(b) by 894 days.

(21) Appl. No.: 17/639,998

(22) PCT Filed: Sep. 10, 2020

(86) PCT No.: PCT/EP2020/075397
§ 371 (c)(1),
(2) Date: Mar. 3, 2022

(87) PCT Pub. No.: WO2021/048313
PCT Pub. Date: Mar. 18, 2021

(65) Prior Publication Data

US 2022/0331209 A1 Oct. 20, 2022

(30) Foreign Application Priority Data

Sep. 13, 2019 (EP) .................................... 19197251

(51) Int. Cl.
*A61K 6/887* (2020.01)
*A61K 6/19* (2020.01)
(Continued)

(52) U.S. Cl.
CPC ................ *A61K 6/887* (2020.01); *A61K 6/19* (2020.01); *A61K 6/40* (2020.01); *A61K 6/62* (2020.01); *A61K 8/20* (2013.01); *A61K 8/466* (2013.01)

(58) Field of Classification Search
CPC .................................. A61K 6/887; A61K 6/62
See application file for complete search history.

(56) References Cited

U.S. PATENT DOCUMENTS 4,261,879 A * 4/1981 Kemper .................. A61K 6/66 523/118
2018/0092811 A1* 4/2018 Klee ....................... C08L 33/10

FOREIGN PATENT DOCUMENTS

CA 2670977 A1 1/2011
CN 107427415 12/2017
(Continued)

OTHER PUBLICATIONS

International Search Report; PCT/EP2020/075397; Oct. 14, 2020 (completed); Oct. 22, 2020 (mailed).
(Continued)

*Primary Examiner* — Michael F Pepitone
(74) *Attorney, Agent, or Firm* — SCHWEGMAN LUNDBERG & WOESSNER, P.A.

(57) ABSTRACT

The present invention is related to a dental composition comprising:
(a) at least one polymerizable monomer having at least one ethylenically unsaturated group;
(b) a radical initiator system comprising
(i) a photosensitizer having an absorption maximum ranging from 400 nm to 800 nm;
(ii) a coinitiator; and
(iii) a compound of the following formula (1):
(Continued)

(I)

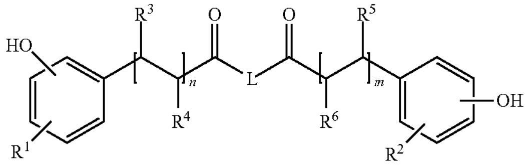

wherein $R^1$ and $R^2$, which may be the same or different, independently represent a hydrogen atom, a $C_{1-6}$ alkyl group, or a $C_{1-6}$ alkoxy group;

$R^3$ and $R^4$, which may be the same or different, independently represent a hydrogen atom, or a $C_{1-6}$ alkyl group, or $R^3$ and $R^4$ may represent a bond so that the carbon atoms to which $R^3$ and $R^4$ are bonded are linked by a double bond;

$R^5$ and $R^6$, which may be the same or different, independently represent a hydrogen atom, or a $C_{1-6}$ alkyl group, or $R^5$ and $R^6$ may represent a bond so that the carbon atoms to which $R^5$ and $R^6$ are bonded are linked by a double bond;

L represents a single bond or a group —CRH—, wherein R may be a hydrogen atom, a $C_{1-6}$ alkyl group, or a $C_{1-6}$ alkoxy group;

n and m, independently are integers of 1 to 6.

15 Claims, 3 Drawing Sheets

(51) Int. Cl.

| | |
|---|---|
| ***A61K 6/40*** | (2020.01) |
| ***A61K 6/62*** | (2020.01) |
| ***A61K 8/20*** | (2006.01) |
| ***A61K 8/46*** | (2006.01) |

(56) References Cited

FOREIGN PATENT DOCUMENTS

| | | |
|---|---|---|
| CN | 109152358 | 1/2019 |
| CN | 114401704 | 4/2022 |
| HK | 40069790 | 10/2022 |
| RU | 2614715 C1 | 3/2017 |
| WO | 2021048313 | 3/2021 |

OTHER PUBLICATIONS

International Preliminary Report on Patentability; PCT/EP2020/075397; Oct. 14, 2020 (completed); Oct. 22, 2020 (mailed).

Written Opinion of the International Searching Authority; PCT/EP2020/075397; Oct. 14, 2020 (completed); Oct. 22, 2020 (mailed).

Crivello et al; "Curcumin: A naturally occurring long-wave length photosensitizer for diaryliodonium salts"; Journal of Polymer Science, Part A: Polymer Chemistry; vol. 43; Sep. 2005; pp. 5217-5231.

Mishra et al; "Curcumin, a novel natural photoinitiator for the copolymerization of styrene and methylmethacrylate"; Journal of Macromolecular Science, Part A—Pure and Applied Chemistry; vol. 42, No. 12; Dec. 2005; pp. 1667-1668.

"Chinese Application Serial No. 202080063751.1, Office Action mailed May 31, 2023", W English Translation, 13 pgs.

"Chinese Application Serial No. 202080063751.1, Office Action mailed Nov. 8, 2023", W English Translation, 13 pgs.

"Chinese Application Serial No. 202080063751.1, Decision of Rejection mailed Apr. 24, 2024", W Machine English Translation, 19 pgs.

"Australian Application Serial No. 2020345012, First Examination Report mailed Mar. 14, 2025", 2 pgs.

* cited by examiner

DENTAL COMPOSITION

CROSS-REFERENCE TO RELATED APPLICATION

This application is a U.S. National Stage Application under 35 U.S.C. 371 from International Application Serial No. PCT/EP2020/075397, filed on Sep. 10, 2020, and published as WO 2021/048313 A1 on Mar. 18, 2021, which claims priority to European Application Ser. No. 19/197,251.2, filed on Sep. 13, 2019, the benefit of priority of each of which is claimed hereby, and each of which are incorporated by reference herein in its entirety.

FIELD OF THE INVENTION

The present invention relates to a dental composition comprising at least one polymerizable monomer having at least one ethylenically unsaturated group; and a radical initiator system.

The present invention is also directed to the use of a compound of the formula (I), (Ia), (Ib) or (Ic) for preparing a dental composition; or for the treatment or prevention of dental disease by restoring hard dental tissue.

BACKGROUND OF THE INVENTION

Polymerizable dental compositions contain a radical polymerizable resin and require therefore a radical initiator system for curing. Such a radical initiator system generates free radicals to initiate the polymerization of the polymerizable resin. Suitable radical initiator systems used in dental compositions may be a photoinitiator system, a redox initiator system or a combination thereof. Photoinitiator systems essentially comprise a photoinitiator compound in combination with a coinitiator compound. The radical initiator system needs to fulfil specific requirements to be useful in dental compositions. For example, radical dental initiator systems require acid resistance, thermal stability, storage stability, and miscibility when incorporated into a dental composition. Simultaneously, radical dental initiator systems require a high polymerization efficiency including a high conversion, good curing rate and depth of cure for providing a useful dental restoration. Finally, radical dental initiator system should not cause coloration so that the color of the cured dental materials resembles the natural color of teeth.

Dental compositions may preferably be cured by light. Light-curable dental compositions are advantageous in handling properties, because the dental composition may be provided as a one-component composition which does not require mixing of multiple components prior to use. A light-curable dental composition requires a photoinitiator system generating reactive species upon exposure to light radiation. Free radicals may be typically produced by either of the two pathways: (1) the photoinitiator compound undergoes excitation by energy absorption and subsequently decomposes into one or more radicals (Norrish type I), or (2) the photoinitiator compound undergoes excitation and the excited photoinitiator compound interacts with a coinitiator compound by either energy transfer or a redox reaction to form free radicals from any of the compounds (Norrish type II).

A high quantum yield of initiation is required for high conversion of the monomers. The quantum yield of initiation indicates the efficiency of the conversion of radiation to reactive radicals. A high conversion can be achieved either by choosing a photoinitiator compound of high photoactivity, or by optimization of the concentration of photoinitiator and stabilizer compound.

Furthermore, it is desirable that the photoinitiator system can be activated at along wavelength to avoid damage of soft tissue during polymerization of the dental composition in the patient's mouth. Accordingly, a visible-light photoinitiator system is required to contain a chromophore group that efficiently absorbs light of the wavelength in the preferable range of from 400 to 800 nm. However, visible-light photoinitiator system are also potentially activated by ambient light. Consequently, the available working time is reduced. An ideal dental composition should have a long working time and a short setting time. The working time of the material towards ambient light may be increased by, for instance, reduction in the concentration of initiators, or increasing the amount of polymerization inhibitor present.

However, both measures can lead to a decrease in quantum efficiency of initiation and a decrease in the physical properties of the light-cured dental material.

Moreover, a visible-light photoinitiator system may also increase the coloration of the photoinitiator system and potentially causes the coloration of the light-cured dental composition.

Accordingly, it is necessary that the chromophore groups undergo photo-bleaching during polymerization so that the coloration of the initiator system disappears in the cured dental composition. Moreover, photobleaching can solve shielding effect and therefore increase the depth of cure for thick samples. The photobleached photoinitiator allows the curing light to transmit through the cured layer and reach the uncured dental composition beneath the cured layer.

Photo-curable dental materials often comprise camphorquinone (CQ) in combination with tertiary aromatic amines (TA) as coinitiator as well as optionally a diphenyliodonium (DPI) salt as reaction accelerator. Latter ternary system is well-known for its high photoinduced polymerization efficiency.

However, CQ suffers from low photoactivity and polymerization efficiency due to its low absorption coefficient at wavelength over 400 nm. Furthermore, an inner shielding effect of the colored CQ, especially at its high concentration, result in unreacted CQ in the sample after curing. The unreacted CQ and monomers can be easily leached by saliva and may cause give rise to toxicological concerns. On the other hand, the unreacted yellow CQ also compromise the esthetics of dental restoration materials and complicate their production.

Furthermore, CQ also suffer from poor photobleaching property, especially when CQ is irradiated only at wavelength over 400 nm, which further aggravate the inner shielding effect and its consequences. Thereby, such known CQ systems result very often in undesired slightly yellow-colored adhesive layers after curing.

Attempts to solve this coloring problem by significantly decreasing the initial CQ concentration has been unsuccessful caused by a finally achieved insufficient curing of the resin matrix.

Objective of the Present Invention

In view of the prior art, it was thus an object of the present invention to provide a new dental composition comprising an initiator system, which shall not exhibit the aforementioned shortcomings of the known prior art dental compositions.

In particular, it was an object of the present invention to provide a dental composition comprising an initiator system, which shall allow to significantly decrease the initially required photosensitizer (such as CQ) concentration without a significant loss of polymerization efficiency and without resulting in yellow-colored adhesive layers after curing (caused by unreacted photoinitiator).

Additionally, it was especially an object of the present invention to provide a photo-curable dental composition which has high polymerization efficiency including simultaneously a high conversion, an adjustable long working time under ambient light, and an adjustable short setting time under dental curing light at wavelength in 400-800 nm.

Furthermore, it was an object to provide a dental composition that can indicate by discoloration the onset of the curing and thereby the region in which the curing light has been already sufficiently applied.

SUMMARY OF THE INVENTION

These objects and also further objects which are not stated explicitly but are immediately derivable or discernible from the connections discussed herein by way of introduction are achieved by a dental composition having all features of claim 1. Appropriate modifications of the dental composition are protected in dependent claims 2 to 13. Further, claim 14 comprises the use of a specific additional compound of a formula (I), (Ia), (Ib) or (Ic) for preparing a dental composition. Claim 15 comprises the use of a specific additional compound of a formula (I), (Ia), (Ib) or (Ic) for the treatment or prevention of dental disease by restoring hard dental tissue.

The present invention accordingly provides a dental composition comprising:

(a) at least one polymerizable monomer having at least one ethylenically unsaturated group; and (b) a radical initiator system comprising (i) a photosensitizer having an absorption maximum ranging from 400 nm to 800 nm; and (ii) a coinitiator:

characterized in that the radical initiator system further comprises (iii) a compound of the following formula (I):

(I)

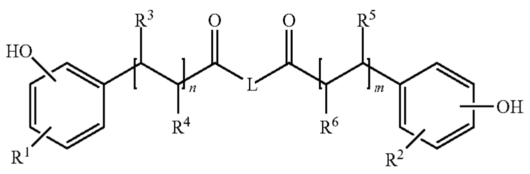

wherein $R^1$ and $R^2$, which may be the same or different, independently represent a hydrogen atom, a $C_{1-6}$ alkyl group, or a $C_{1-6}$ alkoxy group;

$R^3$ and $R^4$, which may be the same or different, independently represent a hydrogen atom, or a $C_{1-6}$ alkyl group, or $R^3$ and $R^4$ may represent a bond so that the carbon atoms to which $R^3$ and $R^4$ are bonded are linked by a double bond; $R^5$ and $R^6$, which may be the same or different, independently represent a hydrogen atom, or a $C_{1-6}$ alkyl group, or $R^5$ and $R^6$ may represent a bond so that the carbon atoms to which $R^5$ and $R^6$ are bonded are linked by a double bond;

L represents a single bond or a group —CRH—, wherein R may be a hydrogen atom, a $C_{1-6}$ alkyl group, or a $C_{1-6}$ alkoxy group;

n and m, independently are integers of 1 to 6.

It is thus possible in an unforeseeable manner to provide a new dental composition comprising an initiator system, which does not exhibit the aforementioned shortcomings of the known prior art dental compositions.

Additionally, the dental composition of the present invention offers an amended initiator system, which allows to significantly decrease the initially required photosensitizer (such as CQ) concentration without a significant loss of polymerization efficiency and without resulting in yellow-colored adhesive layers after curing (caused by unreacted photoinitiator).

Additionally, the dental composition of the present invention has a high polymerization efficiency including simultaneously a high conversion, an adjustable long working time under ambient light, and an adjustable short setting time under dental curing light at wavelength in 400-800 nm.

Furthermore, the dental composition of the present invention can indicate by discoloration the onset of the curing and thereby the region in which the curing light has been already sufficiently applied.

BRIEF DESCRIPTION OF THE FIGURES

For a more complete understanding of the present invention, reference is made to the following Detailed Description of the Invention considered in conjunction with the accompanying figures, in which.

DETAILED DESCRIPTION OF THE INVENTION

Figure 1:
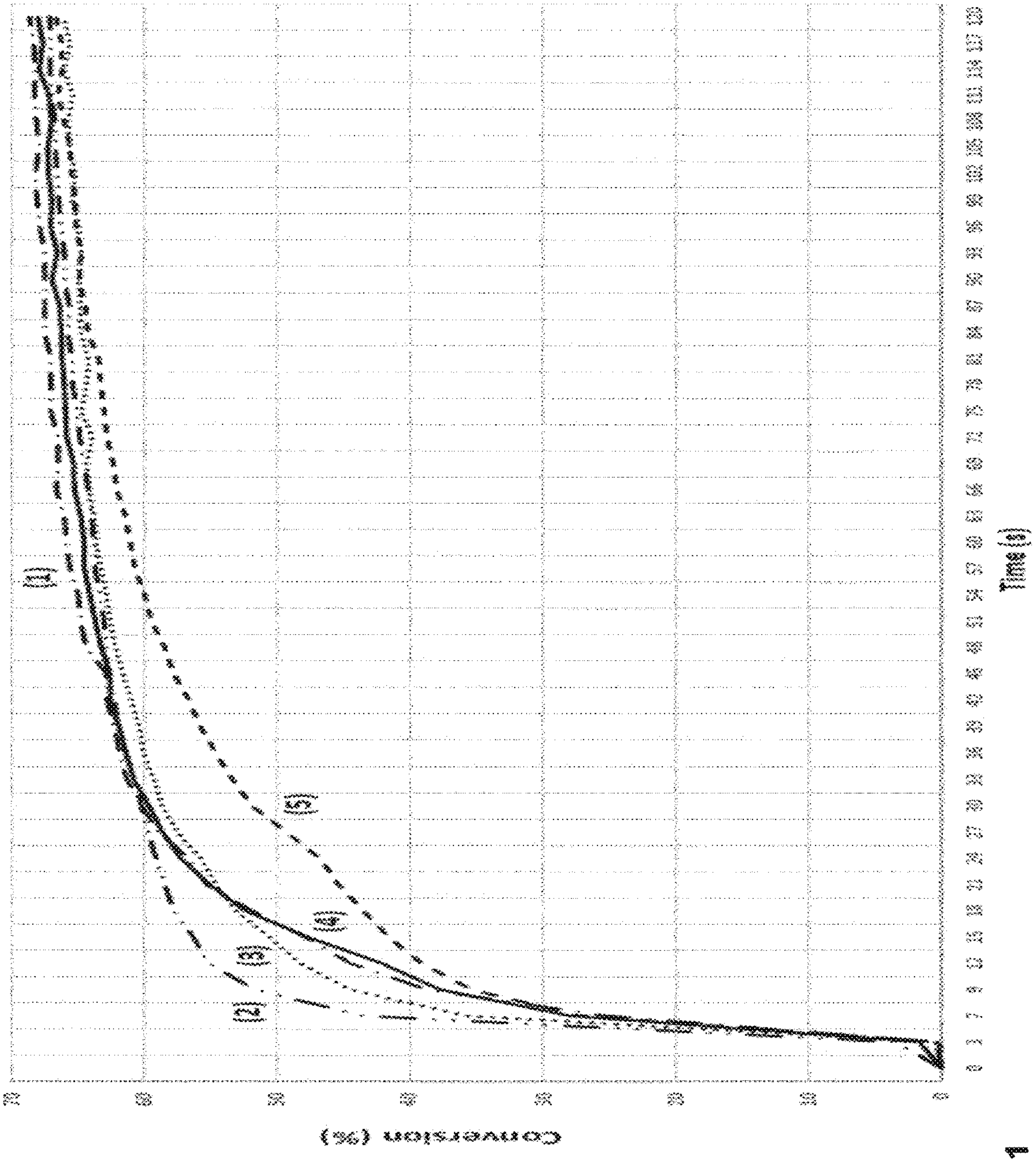
FIG. 1 shows the photopolymerization profiles of reactive functions in the presence of a fixed amount of camphorquinone as photosensitizer and different amounts of curcumin.

The term "alkyl", unless otherwise specified, refers to a monoradical branched or unbranched saturated hydrocarbon chain having from 1 to 18 carbon atoms. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, dodecyl, tetradecyl, and the like.

The term "alkoxy group", unless otherwise specified refers to a monoradical branched or unbranched saturated hydrocarbon chain having from 1 to 18 carbon atoms, wherein at least one carbon atom of such an alkoxy group is substituted by one oxygen atom. Such an alkoxy group is attached by said at least one oxygen atom to a carbon atom of a chemical compound. This term can be exemplified by groups such as methoxy, ethoxy, and the like. That means the term "alkoxy group" is defined in the context of the present invention as any chemist would understand it based on common chemical knowledge.

The term "alkylene", unless otherwise specified refers to a linear saturated divalent hydrocarbon radical of one to four carbon atoms or a branched saturated divalent hydrocarbon radical of three to four carbon atoms, e.g., methylene, ethylene, 2,2-dimethylethylene, propylene, 2-methylpropylene, butylene and the like, preferably methylene, ethylene, or propylene.

The term "aryl" refers to $C_6$-$C_{10}$-membered aromatic, heterocyclic, fused aromatic, fused heterocyclic, biaromatic, or biheterocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those "aryl" groups having heteroatoms in the ring structure may also be referred to as "heteroaryl" or "heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, and combinations thereof.

The term "cycloalkyl" refers to monocyclic or polycyclic cycloalkyl radical. Examples of monocyclic acycloakyl include cyclopropyl, cyclobutyl, cyclopentyl, cyclohexyl, cycloheptyl, and cyclooctyl. Examples of polycyclic cycloalkyl radical include, for example adamantyl, norbornyl, decalinyl, 7,7-dimethyl-bicyclo[2.2.1]heptanyl, tricyclo [5.2.1.02,6]decyl and the like.

The term "(meth)acrylate" in the context of the present disclosure is meant to refer to the acrylate as well as to the corresponding methacrylate.

The term "(meth)acrylamide" in the context of the present disclosure is meant to include acrylamide and methacrylamide.

The term "polymerizable monomer" in the context of the present disclosure means any monomer capable of radical polymerization. The polymerizable monomer includes at least one ethylenically unsaturated groups. The at least one ethylenically unsaturated groups include vinyl, allyl, acryl, methacryl, and styryl.

The term "a polymerizable monomer having at least one ethylenically unsaturated group" and "ethylenically unsaturated monomers" may be used interchangeably.

The term "radical initiator system" in the context of the present disclosure means any system comprising a photosensitizer and at least one coinitiator forming free radicals when activate by thermal or light and/or ambient redox conditions, whereby polymerization of polymerizable monomer is initiated.

The term "coinitiator" in the context of the present disclosure means a compound that does not essentially absorb when exposed with UV radiation or visible light but forms free radicals together with the photosensitizers used according to the present disclosure.

The term "photosensitizer" in the context of the present disclosure means a compound which can absorb radiation of a wavelength in the range of 400 to 800 nm, when it is exposed but which cannot by itself, i.e. without the addition of coinitiators, form free radicals. Photosensitizers used in the present disclosure have to be capable of interacting with the coinitiators used in the present disclosure. The terms "photosensitizer" and "photoinitiators" are equivalents in the context of the present invention.

The Polymerizable Monomers

The dental composition of the present disclosure comprises one or more polymerizable monomers having at least one ethylenically unsaturated group.

Polymerizable monomers may be acrylates, methacrylates, ethylenically unsaturated compounds, carboxyl group-containing unsaturated monomers, C2-8 hydroxyl alkyl esters of (meth)acrylic acid, C1-24 alkyl esters or cycloalkyl esters of (meth)acrylic acid, C2-18 alkoxyalkyl esters of (meth)acrylic acid, olefins or diene compounds, monoesters/diesters, monoethers, adducts, vinyl monomer, styryl monomer, TPH resin, SDR Resin, PBA resins and/or BPA-free resins.

Examples of specific acrylate monomer include, but are not limited to, methyl acrylate, ethyl acrylate, propyl acrylate, isopropyl acrylate, 2-hydroxyethyl acrylate, hydroxypropyl acrylate, tetrahydrofurfuryl acrylate, glycidyl acrylate, glycerol mono- and di-acrylate, ethylene glycol diacrylate, polyethyleneglycol diacrylate, neopentyl glycol diacrylate, trimethylolpropane triacrylate, mono-, di-, tri-acrylate, mono-, di-, tri-, and tetra-acrylates of pentaerythritol and dipentaerythritol, 1,3-butanediol diacrylate, 1,4-butanedioldiacrylate, 1,6-hexanediol diacrylate, 2,2'-bis[3 (4-phenoxy)-2-hydroxypropane-1-acrylate]propane, 2,2'-bis (4-acryloxyphenyl)propane, 2,2'-bis[4(2-hydroxy-3-acryloxy-phenyl)]propane, 2,2'-bis(4-acryloxyethoxyphenyl)propane, 2,2'-bis(4-acryloxypropoxyphenyl)propane,2,2'-bis(4-acryloxydiethoxyphenyl)propane, 2'-bis[3(4-phenoxy)-2-hydroxypropane-1-acrylate]propane, and dipentaerythritol pentaacrylate esters.

Examples of specific conventional methacrylate monomer include, but are not limited to, methyl methacrylates, ethyl methacrylate, propyl methacrylate, isopropyl methacrylate, tetrahydrofurfuryl methacrylate, glycidyl methacrylate, the diglycidyl methacrylate of bis-phenol A (2,2-Bis[4-(2-hydroxy-3-methacryloxypropoxy)phenyl]propane) (Bis-GMA), 4,4,6,16 (or 4,6,6,16)-tetramethyl-10,15-dioxo-11, 14-dioxa-2,9-diazaheptadec-16-enoicacid 2-[(2-methyl-1-oxo-2-propen-1-yl)oxy]ethyl ester (CAS no. 72869-86-4) (UDMA), glycerol mono- and dimethacrylate, ethyleneglycol dimethacrylate, polyethyleneglycol dimethacrylate, triethylene glycol dimethacrylate (TEGDMA), neopentylglycol dimethacrylate, trimethylol propane trimethacrylate, mono-, di-, tri-, and tetra-methacrylates of pentaerythrital and dipentaerythritol, 1,3-butanediol dimethacrylate, 1,4-butanediol dimethacrylate, Bis[2-(methacryloyloxy)ethyl]phosphate (BisMEP),1,6-hexanediol dimethacrylate, 2-2'-bis(4-methacryloxyphenyl)propane, 2,2-bis[4 (2-hydroxy-3-methacryloxy-phenyl)]propane, 2,2'-bis(4-methacryloxyethoxyphenyl)propane, 2,2'-bis(4-methacryloxypropoxyphenyl)propene, 2,2'-bis(4-methacryloxydiethoxyphenyl)propane, 2,2'-bis[3(4-phenoxy)-2-hydroxypropane-1-methacrylate]propane, di-2-methacryloyloxyethyl hexamethylene dicarbamate, di-2-methacryloyloxyethyl trimethylhexamethylene dicarbamate, di-2-methacryloyl oxyethyl dimethylbenzene dicarbamate, methylene-bis-2-methacryloxyethyl-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-Methyl-2-methacryloxyethyl-dimethylbenzene dicarbamate, di-1-methyl-2-methacryloxyethyl-dimethylcyclohexane dicarbamate, methylenebis-1-methyl-2-methacryloxyethyl- 4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, and methylene-bis-1-chloromethyl-2-methacryloxyethyl-4-cyclohexyl carbamate.

Examples of ethylenically unsaturated compounds include, but are not limited to, acrylic acid esters, methacrylic acid esters, hydroxy-functional acrylic acid esters, hydroxy-functional methacrylic acid esters, halogen, and hydroxy containing methacrylic acid esters and combinations thereof. Such free radically polymerizable compound include n-, sec-, or t-buty methacrylate, hexyl methacrylate, 2-ethylhexyl methacrylate, octylmethacrylate, decyl methacrylate, lauryl methacrylate, cyclohexyl methacrylate, stearyl(meth)acrylate, allyl(meth)acrylate, glycerol tri (meth)acrylate, diethyleneglycol di(meth)acrylate, triethyleneglycol di(meth)acrylate, 1,3-propanediol di(meth)acrylate, 1,2,4-butanetriol tri(meth)acrylate, 1,4-cyclohexanediol di(meth)acrylate, pentaerythritol tetra (meth)acrylate, sorbitol hex(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate tri(meth)acrylate; urethane (meth)acrylates; ((di)urethane dimethacrylate), the bis-(meth)acrylates of polyethylene glycols, and chlorine-, bromine-, fluorine-, and hydroxyl group containing monomers, for example, 3-chloro-2-hydroxylpropyl (meth)acrylate, and reaction product of Bisphenol-A-Glycidylmethacrylate (BisGMA) and a hexamethylene diisocyanate (HMDI).

Examples of carboxyl group-containing unsaturated monomers include, but are not limited to, acrylic acid, methacrylic acid, crotonic acid, itaconic acid, maleic acid, and fumaric acid. Examples of C2-8 hydroxyl alkyl esters of (meth)acrylic acid include, but are not limited to, 2-hydroxylethyl (meth)acrylate, 2-hydroxylpropyl (meth)acrylate, 3-hydroxypropyl (meth)acrylate, and hydroxybutyl (meth) acrylate. Examples of C2-18 alkoxyalkyl esters of (meth) acrylic acid include, but are not limited to, methoxybutyl methacrylate, methoxyethyl methacrylate, ethoxyethyl methacrylate, and ethoxybutyl methacrylate. Specifically, acrylate and methacrylates may be

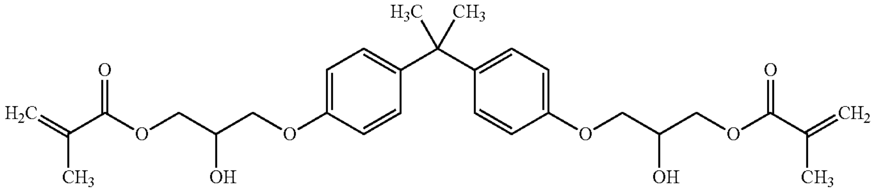

BisGMA

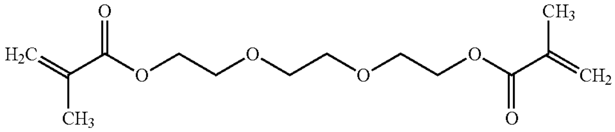

TEGDMA

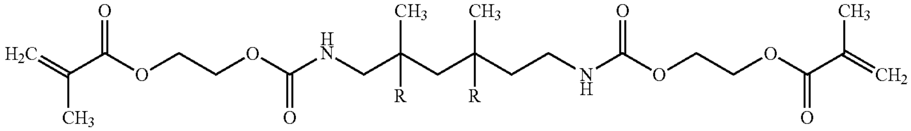

R = H or $CH_3$ (-1 or 1)

UDMA

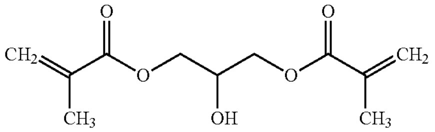

GDM

Specifically, methacrylamide may be bis-(meth)acrylamides, such as N,N'-diallyl-1,4-bisacrylamido-(2E)-but-2-en (BAABE) having the structural formula

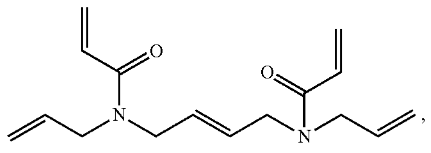 [SMILES: C=CCN(C/C=C/CN(CC=C)C(=O)C=C)C(=O)C=C]

and/or

N,N'-diethyl-1,3-bisacrylamido-propan (BADEP) having the structural formula

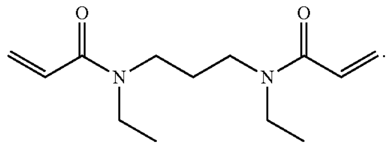 [SMILES: C=CC(=O)N(CC)CCCN(CC)C(=O)C=C]

A Radical Initiator System

The dental composition of the present disclosure includes a radical initiator system. Said radical initiator system includes at least one photoinitiator being in the form of a binary or a tertiary system. A binary system includes at least a photosensitizer and a coinitiator. A tertiary system comprises additionally an iodonium, sulfonium or phosphonium salt.

The present invention is based on the recognition that a compound of formula (I), particularly of a formula (Ia), (Ib) or (Ic), shows different photochemical properties in the ground state and excited states.

Furthermore, it is surprisingly found that a dental composition comprising a compound of formula (I), particularly of a formula (Ia), (Ib) or (Ic), requires only reduced amount of photosensitizer for curing reaction with a better polymerization efficiency in terms of conversion rate and curing rate. Therefore, leaching problems of the unreacted photoinitiator may also have been reduced or avoided.

Moreover, the present invention is also based on the recognition that a compound of formula (I), particularly of a formula (Ia), (Ib) or (Ic), has excellent photobleaching properties. Therefore, discoloration take place upon the curing of the dental composition, so that a dental practitioner can observe the onset of curing based on the color change in the dental composition. Besides, the singlet oxygen generated by the compound of formula (I) can also react with other chromophores, such as unreacted photoinitiator, in the composition and lead to its photo-bleaching and/or discoloration. Consequently, the cured dental composition has a color that is close to the natural teeth and does not have coloration problem.

In a preferred embodiment, the radical initiator system comprises an 1,2-diketone compound as photosensitizer, and a tertiary amine, an aromatic phosphine, a germanium hydride, a sulfinic acid salt or a sulfonic acid salt as coinitiator.

Suitable 1,2-diketone compounds may be selected from the group consisting of camphorquinone, benzil, 2,2'-33- and 4,4'-dihydroxybenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone, and acenaphthoquinone. Such suitable 1,2-diketone compounds preferably absorb light within a range of about 400 nm to about 520 nm, preferably about 450 nm to about 500 nm.

Suitable tertiary amines may be selected from the group consisting of trialkanolamine, 4-N,N-dialkylaminobenzonitrile, alkyl N,N-dialkylaminobenzoate, alkyl N,N-dialkylaminobenzoate, N,N-dialkylaminoethyl alkylacrylate and isoamyl 4-N,N-dialkylaminobenzoate, N,N-dialkylaniline, N,N-dialkyltoluidine, N,N-dialkylotoluidine, dialkylaminoanisole, 1 or 2-dialkylaminonaphthalene.

In particular, the tertiary amine may be selected from the group consisting of triethanolamine, alkyl 4-N,N-dialkylaminobenzoate, ethyl 4-N,N-dialkylaminobenzoate, 4-N,N-dialkylaminoethyl methacrylate, isoamyl 4-N,N-dialkylaminobenzoate and 4,4'-N,N-bis(dialkylamino)benzophenone.

Herein, the alkyl group may represent a straight chain, branched or cyclic alkyl group. Furthermore, if more than one alkyl group is comprised, the alkyl groups may be the same or different, preferably they are the same. Preferably, the alkyl group is a C1-6 alkyl group, more preferably a C1-4 alkyl group. Most preferably, the alkyl group is a methyl or ethyl group.

Particular preferred tertiary amines may be selected from the group consisting of triethanolamine, 4-N,N-dimethylaminobenzonitrile, methyl N,N-dimethylaminobenzoate, ethyl N,N-dimethylaminobenzoate (DMABE), N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. More preferred tertiary amines may be selected from the group consisting of triethanolamine, methyl 4-N,N-dimethylaminobenzoate, ethyl 4-N,N-dimethylaminobenzoate (DMABE), 4-N,N-dimethylaminoethyl methacrylate, isoamyl 4-N,N-dimethylaminobenzoate and 4,4'-N,N-bis(dimethylamino)benzophenone. Most preferably, the tertiary amine coinitiator is ethyl 4-N,N-dimethylaminobenzoate (DMABE) or 4-dimethylaminobenzonitrile (DMABN).

In a further embodiment, the radical initiator system comprises camphorquinone as photosensitizer a tertiary amine as coinitiator; and a compound of the following formula (Ia):

(Ia)

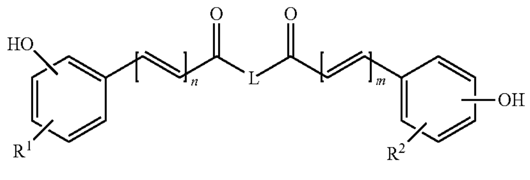

wherein $R^1$ and $R^2$, which may be the same or different, independently represent a hydrogen atom, a $C_{1-6}$ alkyl group, or a $C_{1-6}$ alkoxy group;

L represents a single bond or a group —CRH—, wherein R may be a hydrogen atom, a $C_{1-6}$ alkyl group, or a $C_{1-6}$alkoxy group;

n and m, independently are integers of 1 to 6.

In a further embodiment, the radical initiator system comprises camphorquinone as photosensitize; a tertiary amine as coinitiator; and a compound of the following formula (Ib):

(Ib)

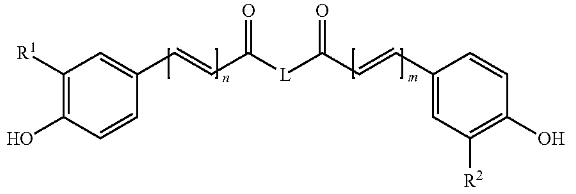

wherein $R^1$ and $R^2$, which may be the same or different, independently represent a hydrogen atom, a $C_{1-6}$ alkyl group, or a $C_{1-6}$ alkoxy group;

L represents a single bond or a group —CRH—, wherein R may be a hydrogen atom, a $C_{1-6}$ alkyl group, or a $C_{1-6}$ alkoxy group;

n and m, independently are integers of 1 to 6.

In a further embodiment, the radical initiator system comprises camphorquinone as photosensitizer, a tertiary amine as coinitiator; and a compound of the following formula (Ic):

(Ic)

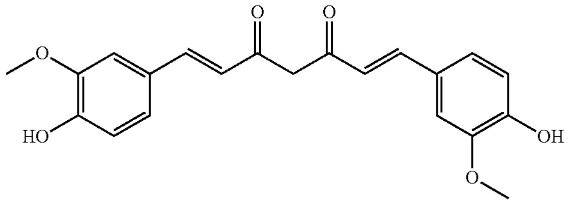

Said compound (Ic) is known as curcumin (herein also referred to as CCM).

In one embodiment, the ratio of the amount of the photosensitizer to the amount of the compound of the formula (I), (Ia), (Ib) or (Ic) is ranging from 200:1 to 1:1; preferably ranging from 100:1 to 1:1; and more preferably ranging from 50:1 to 1:1.

In one embodiment, the amount of the compound of the formula (I), (Ia), (Ib) or (Ic) is ranging from 0.01 to 1.2 percent by weight, preferably ranging from 0.02 to 0.9 percent by weight, and more preferably ranging from 0.03 to 0.7 percent by weight, based on the total weight of the dental composition.

In one embodiment, the amount of the photosensitizer is ranging from 0.1 to 3 percent by weight, preferably ranging from 0.3 to 2.4 percent by weight, and more preferably ranging from 0.6 to 1.6 percent by weight, based on the total weight of the dental composition.

In another preferred embodiment, the dental composition further comprises an additive selected from iodonium salts, phosphonium salts, and sulfonium salts; preferably wherein said additive is an iodonium salt.

In particular, said additive is selected from diaryl iodonium salts, triaryl sulfonium salts, and tetraaryl or tetraalkyl phosphonium salts.

For example, diaryl iodonium salt may be selected from the group consisting of (4-methylphenyl)[4-(2-methylpropyl)phenyl]iodonium hexafluoroantimonate, include (4-methylphenyl)[4-(2-methylpropyl)phenyl]iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl) iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborate, phenyl-2-thienyliodonium hexafluorophosphate, 3,5-dimethylpyrazolyl-4-phenyliodonium hexafluorophosphate, DPI hexafluoroantimonate, 2,7-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, Bis-(4-t-butylphenyl)iodonium hexafluorophosphate (SC938), di(4-acetamidophenyl)iodonium hexafluorophosphate, di(2-benzothienyl)iodonium hexafluorophosphate, and DPI hexafluorophosphate.

Particularly preferred diaryl iodonium compounds include diphenyliodonium (DPI) hexafluorophosphate, di(4-methylphenyliodonium (Me2-DPI) hexafluorophosphate, diaryliodonium hexafluoroantimonate, (4-methylphenyl)[4-(2-methylpropyl)phenyl]iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl)phenyl]iodonium tetrafluoroborate, 4-octyloxyphenyl phenyliodonium hexafluoroantimonate, Bis-(4-t-butylphenyl)-iodonium hexafluorophosphate (SC938), 4-(2-hydroxytetradecyloxyphenyl)phenyliodonium hexafluoroantimonate, and 4-isopropyl-4'-methyldiphenyliodonium borate.

According to a particularly preferred embodiment, the iodonium compound is (Me2-DPI) hexafluorophosphate or Bis-(4-t-butylphenyl)-iodonium hexafluorophosphate (SC938).

A preferred triaryl sulfonium salt is S-(phenyl)thianthrenium hexafluorophosphate.

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

In a preferred embodiment thereof, the amount of the additive is ranging from 0.01 to 3 percent by weight, preferably ranging from 0.25 to 2 percent by weight, and more preferably ranging from 0.5 to 1.2 percent by weight, based on the total weight of the dental composition.

In one embodiment, the amount of the radical initiator system is ranging from 0.1 to 10 percent by weight, preferably ranging from 0.7 to 7 percent by weight, and more preferably ranging from 1.5 to 4.5 percent by weight, based on the total weight of the dental composition.

In one embodiment, the amount of the coinitiator is ranging from 0.1 to 3 percent by weight, preferably ranging from 0.3 to 2.4 percent by weight, and more preferably ranging from 0.5 to 1.5 percent by weight, based on the total weight of the dental composition.

In one embodiment, the dental composition is selected from a dental adhesive composition, a dental composite, a root canal filling composition, a dental pit and fissure sealer, a dental primer, a dental sealant, a dental varnish, a dental infiltrant or a resin modified dental cement composition.

The present invention also provides a use of a compound of the formula (I), (Ia), (Ib) or (Ic) for preparing a dental composition according to the present invention.

Additionally, the present invention also provides a use of a compound of the formula (I), (Ia), (Ib) or (Ic) for the treatment or prevention of dental disease by restoring hard dental tissue with a dental composition according to the present invention.

The present invention thus addresses the problem of improving known dental compositions having a radical initiator system comprising a photosensitizer and a coinitiator, which allows to significantly decrease the initially required photosensitizer (such as CQ) concentration without a significant loss of polymerization efficiency and without resulting in yellow-colored adhesive layers after curing (caused by unreacted photoinitiator).

The following non-limiting examples are provided to illustrate embodiments of the present invention and to facilitate understanding of the invention but are not intended to limit the scope of the invention, which is defined by the claims appended hereto.

Example 1

The polymerization of a Prime & Bond Active liquid in presence of CQ/CCM/DMABN/SC938 as radical initiator system has been investigated. Herein, different amounts of curcumin (CCM) has been used while keeping the amounts of CQ, DMABN and SC938 constant (s.a. FIG. 1).

Herein, FIG. 1 shows the respective photopolymerization profiles of reactive functions in the presence of a fixed amount of camphorquinone as photosensitizer and different amounts of curcumin (under air; SmartLite Focus 300 mW·cm−2, in monomer Prime & Bond Active, the irradiation starts at t=5 s till t=120 s, thickness=15 μm).

1. CQ/CCM/DMABN/SC938 (1/0.5/1/1% w/w)
2. CQ/CCM/DMABN/SC938 (1/0.2/11/1% w/w)
3. CQ/CCM/DMABN/SC938 (1/0.1/1/1% w/w)
4. CQ/CCM/DMABN/SC938 (1/0.05/1/1% w/w)
5. CQ/DMABN/Me2-DPI as reference system (1.55/0.65/0.75% w/w).

Remarkably, the performances of the system CQ/CCM/DMABN/SC938 to initiate the radical polymerization of Prime & Bond Active as dental resin upon irradiation by a blue dental LED light (SmartLite Focus; 300 mW·cm$^2$) overcome the performance of the reference system CQ/DMABN/Me2-DPI in the same conditions, showing the role and effect of CCM as photoinitiator when combined with camphorquinone (s.a. FIG. 1).

Example 2

As CCM was proposed as a new additive when combined with CQ, it is also possible to decrease the amount of CQ by adding CCM while keeping the same polymerization performances. For example, the polymerization of Prime & Bond Active liquid in presence of CQ/CCM/DMABN/SC938 as radical initiator system comprising different amounts of CQ is shown in FIG. 2.

Figure 2:
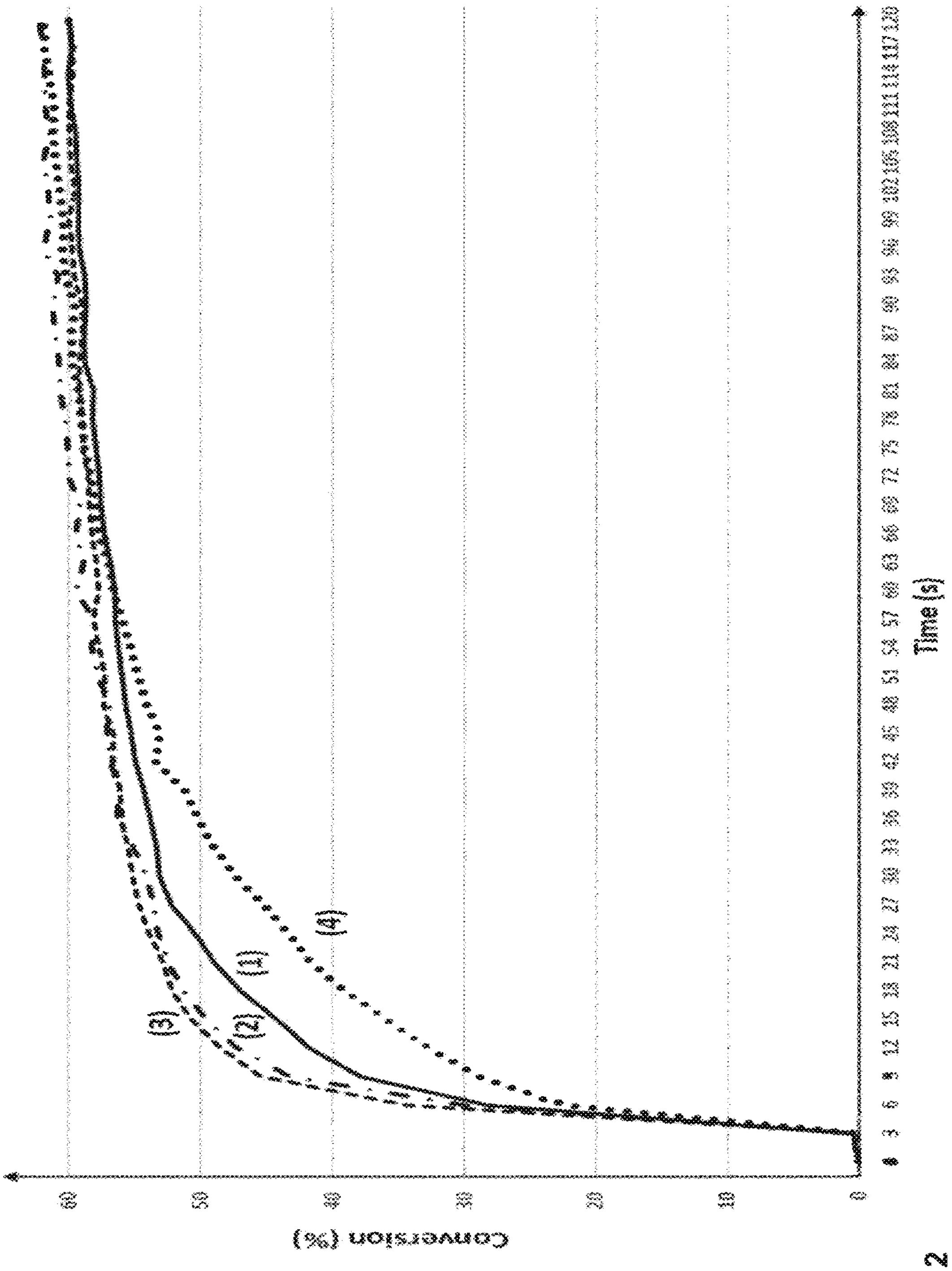
FIG. 2 shows the photopolymerization profiles of reactive functions in the presence of different amounts of camphorquinone as photosensitizer and a fixed amount of curcumin.

FIG. 2 shows the photopolymenzation profiles of reactive functions in the presence of camphorquinone as photoinitiator (under air; SmartLite Focus 300 mW·cm−2, in monomer Prime & Bond Active, the irradiation starts at t=5 s till t=120 s, thickness=15 μm)

1. CQ/CCM/DMABN/SC938 (1.55/0.05/0.65/0.75% w/w);
2. CQ/CCM/DMABN/SC938 (1.00/0.0510.6510.75% w/w);
3. CQ/CCM/DMABN/SC938 (0.7/0.05/0.65/0.75% w/w);
4. CQ/DMABN/Me2-DPI as reference system (1.55/0.65/0.75% w/w).

Remarkably, the amount of CQ can be reduced from 1.55 to 0.7% in presence of 0.05% of CCM while maintaining the same photopolymerization performances as for the reference CQ/DMABN/Me2-DPI (1.55/0.6510.75% w/w).

Example 3

CCM can be used as coinitiator with CQ in the system CQ/CCM/DMABN/SC938 for the polymerization of thin samples (15 μm) of Prime & Bond Active under air and under irradiation with the SmartLite Focus (300 mW·cm−2).

Figure 3:
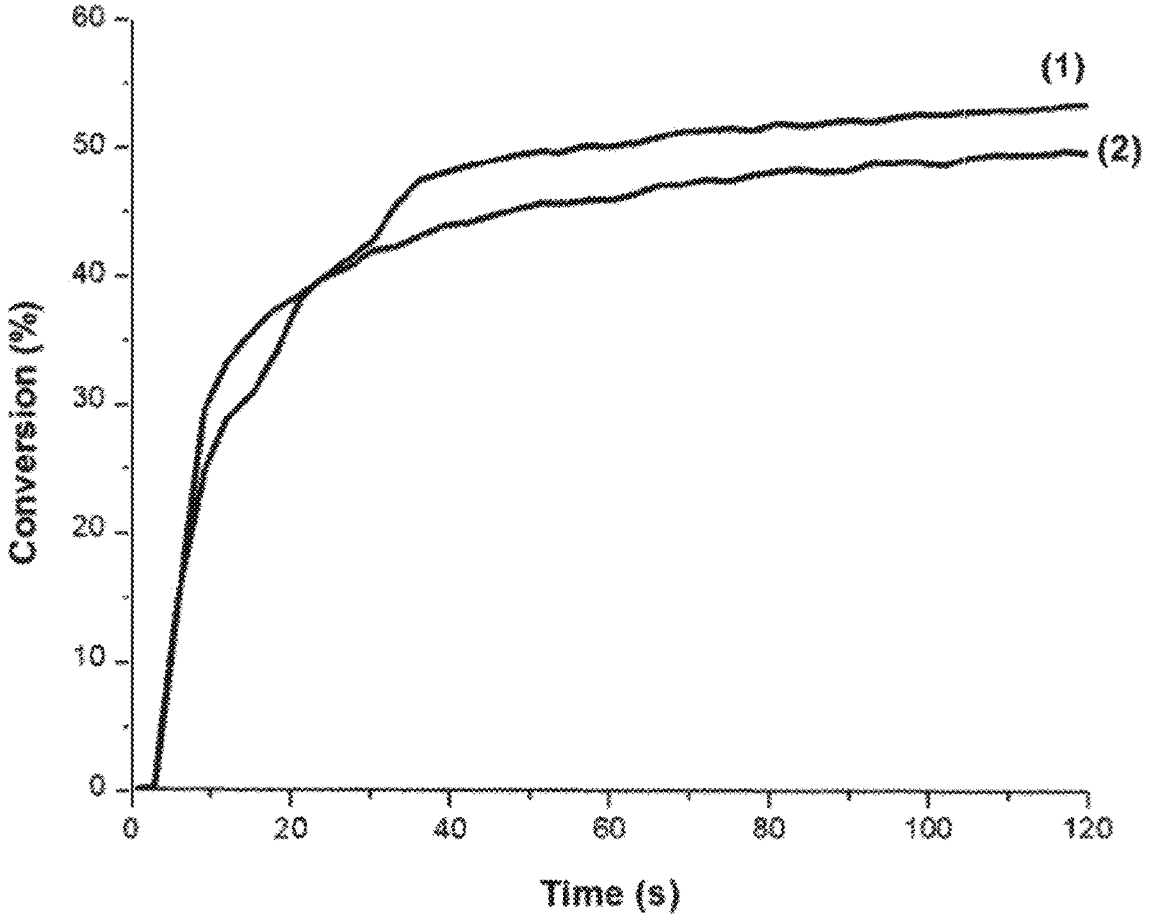
FIG. 3 shows the photopolymerization profiles of reactive functions in the presence of camphorquinone as photosensitizer with and without the presence of curcumin.

FIG. 3 shows the photopolymenzation profiles of reactive functions in the presence of camphorquinone as photoinitiator (under air; SmartLite Focus 300 mW·cm−2, in monomer Prime & Bond Active, the irradiation starts at t=5 s till t=120 s, thickness=15 μm)

1. CQ/CCM/DMABN/SC938 (0.7/0.05/0.65/0.75% w/w)
2. CQ/CCM/DMABN/SC938 as reference system (0.7/0.0010.65/0.75% w/w).

Remarkably, the system CQ/CCM/DMABN/SC938 presents enhanced polymerization performances compared to the reference system CQ/DMABN/SC938 clearly demonstrating the high synergy between CQ and CCM for high performance initiating system (better than CQ alone).

Example 4

The system CQ/CCM/DMABN/SC938 presents also exceptional bleaching properties upon irradiation with the blue dental LED. Nevertheless, as CCM is orange colored, better bleaching properties have been obtained for the system CQ/CCM/DMABN/SC938 (1/0.05/1/1% w/w) than those of the reference system CQ/DMABN/Me2-DPI (1.55/0.6510.75% w/w).

Photos of the samples before and after polymerization have been taken. Based on these photos the L, a, and b values have been measured for each sample after irradiation. The respective polymerization has been executed under air; SmartLite Focus 300 mW·cm−2, in monomer Prime & Bond Active, the irradiation starts at t=5 s till t=120 s, thickness=15 μm.

Invention: CQ/CCM/DMABN/SC938: L=67+/−2; a=−2+/−2; b=3+/−2

Prior Art: CQ/DMABN/Me2-DPI: L=66+/−2; a=−2+/−2; b=5+/−2

Thus, CCM can be used as a polymerization indicator i.e. the irradiated areas for which the light intensity is high enough to initiate an efficient polymerization are fully bleached. This visual inspection can be used by the dentist to know the well polymerized areas (bleached ones).

Example 5

Remarkably, adding 0.05% of CCM and decreasing the amount of CQ from 1.55 to 0.7% leads to exceptional bleaching properties and does not affect the final color properties after polymerization whereas the sample before irradiation is more colored in presence of CCM. The main advantage of this initial coloration is that the change of color upon polymerization can be followed by naked eye with CCM (the Ab is much higher than without CCM but with the advantage of a full final bleaching); CCM acts as a colored visible indicator of polymerization. CCM is also a light intensity indicator the higher the light intensity in a given zone, the better the change of color and bleaching of CCM.

Prior Art CQ/DMABN/SC938 (1.55/0.6510.75% w/w)

Invention: CQ/CCM/DMABN/SC938 (0.7/0.05/0.65/0.75% w/w).

Photos of the samples before irradiation and after different period of irradiations (10 s and 20 s) have been taken. The irradiated areas for which the light intensity is high enough to initiate an efficient polymerization are fully bleached. This visual inspection can be used by the dentist to know if the light intensity is high enough for an efficient polymerization in a given areas. Based on these photos the L, a, and b values have been measured for each sample after irradiation. The respective polymerization has been executed under air; SmartLite Focus 300 mW·cm−2, in monomer Prime & Bond Active, the irradiation time t=10 s and t=20 s, thickness=15 μm.

Prior Art (before irradiation): L=67+/−2; a=−5+/−2; b=6+/−2

Prior Art (after 10 s of irradiation): L=66+/−2; a=2+/−2: b=2+/−2; Δb=4

Prior Art (after 20 s of irradiation): L=66+/−2; a=−2+/−2; b=2+/−2; Δb=4

Invention (before irradiation): L=72+/−2; a=−13+/−2; b=36+/−2

Invention (after 10 s of irradiation): L=67+/−2; a=−5+/−2; b=3+/−2; Δb=33

Invention (after 20 s of irradiation): L=67+/−2; a=−2+/−2; b=3+/−2; Δb=33

While the principles of the invention have been explained in relation to certain particular embodiments, and are provided for purposes of illustration, it is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the appended claims.

The invention claimed is:

1. Dental composition comprising:

(a) at least one polymerizable monomer having at least one ethylenically unsaturated group; and (b) a radical initiator system comprising (i) a photosensitizer having an absorption maximum ranging from 400 nm to 800 nm, which is camphorquinone; and (ii) a coinitiator, which is a tertiary amine;

characterized in that the radical initiator system further comprises (iii) a compound of the following formula (Ic):

(Ic)

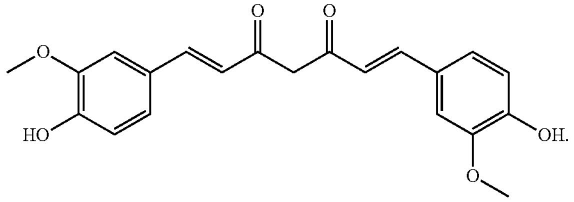

in a range of from about 0.01 to about 1.2 percent based on the total weight of the dental composition.

2. Dental composition according to claim 1, characterized in that the ratio of the amount of the photosensitizer to the amount of the compound of the formula (Ic) is ranging from 200:1 to 1:1.

3. Dental composition according to claim 1, characterized in that the amount of the compound of the formula (Ic) is ranging from 0.05 to 1.2 percent by weight based on the total weight of the dental composition.

4. Dental composition according to claim 1, characterized in that the amount of the photosensitizer is ranging from 0.1 to 3 percent by weight based on the total weight of the dental composition.

5. Dental composition according to claim 1 characterized in that the dental composition further comprises an additive selected from iodonium salts, phosphonium salts, and sulfonium salts.

6. Dental composition according to claim 5 characterized in that the amount of the additive is ranging from 0.01 to 3 percent by weight based on the total weight of the dental composition.

7. Dental composition according to claim 1 characterized in that the amount of the radical initiator system is ranging from 0.1 to 10 percent by weight based on the total weight of the dental composition.

8. The dental composition according to claim 1 characterized in that the amount of the coinitiator is ranging from 0.1 to 3 percent by weight based on the total weight of the dental composition.

9. Dental composition according to claim 1, characterized in that the dental composition is selected from a dental adhesive composition, a dental composite, a root canal filling composition, a dental pit and fissure sealer, a dental primer, a dental sealant, a dental varnish, a dental infiltrant or a resin modified dental cement composition.

10. A method of treatment or prevention of dental disease comprising restoring hard dental tissue with a dental composition according to claim 1.

11. Dental composition according to claim 1, wherein the compound of formula (Ic) exhibits photobleaching properties upon exposure to light radiation, resulting in color change during polymerization.

12. Dental composition according to claim 1, wherein the compound of formula (Ic) acts as a visible indicator of polymerization through color change from colored to substantially colorless upon curing.

13. Dental composition according to claim 1, wherein the dental composition is a cured dental composition and exhibits substantially no yellow coloration after polymerization due to photobleaching of the compound of formula (Ic).

14. Dental composition according to claim 1, wherein the photosensitizer which is camphorquinone ranges from about 0.7 to about 1.55 percent based on the total weight of the dental composition and the compound of formula (Ic) ranges from about 0.05 to about 0.2 percent based on the total weight of the dental composition.

15. Dental composition according to claim 14, wherein the photosensitizer which is camphorquinone is present at about 0.7 percent based on the total weight of the dental composition and the compound of formula (Ic) is present at about 0.05 percent based on the total weight of the dental composition.

* * * * *